(12) United States Patent
Zeller et al.

(10) Patent No.: US 7,069,066 B2
(45) Date of Patent: Jun. 27, 2006

(54) BONE DENSITOMETER PROVIDING IMPROVED LONGITUDINAL STUDIES

(75) Inventors: Scott Steven Zeller, Madison, WI (US); Grant Morey Stevens, Verona, WI (US); Paul Eugene Markwardt, Verona, WI (US); Russell Harry Nord, Ft. Atkinson, WI (US); Robert Washkenko, Madison, WI (US); David Lowry Ergun, Verona, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/972,902

(22) Filed: Oct. 25, 2004

(65) Prior Publication Data
US 2005/0096527 A1    May 5, 2005

Related U.S. Application Data

(63) Continuation-in-part of application No. 10/065,109, filed on Sep. 18, 2002, now Pat. No. 6,892,088.

(51) Int. Cl.
*A61B 5/05* (2006.01)
*G01B 15/02* (2006.01)

(52) U.S. Cl. .................... 600/407; 378/50; 387/89
(58) Field of Classification Search ........... 600/407, 600/1, 408; 606/2, 20, 27, 32; 378/45, 50, 378/88, 89
See application file for complete search history.

(56) References Cited

U.S. PATENT DOCUMENTS

| | | | |
|---|---|---|---|
| 4,858,128 A | 8/1989 | Nowak | |
| 4,864,594 A * | 9/1989 | Inbar et al. | 378/5 |
| 4,922,915 A | 5/1990 | Arnold et al. | |
| 5,003,980 A | 4/1991 | Loo et al. | |
| 5,090,040 A * | 2/1992 | Lanza et al. | 378/62 |
| 5,138,553 A * | 8/1992 | Lanza et al. | 600/407 |
| 5,306,306 A | 4/1994 | Bisek et al. | |
| 5,348,009 A | 9/1994 | Ohtomo et al. | |
| 5,480,439 A | 1/1996 | Bisek et al. | |
| 5,594,775 A * | 1/1997 | Hangartner | 378/207 |
| 5,712,892 A * | 1/1998 | Weil et al. | 378/54 |
| 6,002,959 A | 12/1999 | Steiger et al. | |
| 6,038,281 A | 3/2000 | Mazess | |
| 6,160,866 A | 12/2000 | Mazess et al. | |
| 6,246,745 B1 | 6/2001 | Bi et al. | |
| 6,320,931 B1* | 11/2001 | Arnold | 378/56 |
| 6,418,183 B1 | 7/2002 | Fox et al. | |
| 6,436,201 B1 | 8/2002 | Sugita et al. | |
| 6,438,201 B1 | 8/2002 | Mazess et al. | |
| 6,490,339 B1* | 12/2002 | Mitchell et al. | 378/62 |
| 6,510,197 B1* | 1/2003 | Mitchell et al. | 378/62 |
| 6,690,761 B1* | 2/2004 | Lang et al. | 378/56 |
| 6,811,310 B1* | 11/2004 | Lang et al. | 378/169 |

* cited by examiner

*Primary Examiner*—Daniel Robinson
(74) *Attorney, Agent, or Firm*—Quarles & Brady LLP; Carl Horton

(57) ABSTRACT

An x-ray densitometry system provides improved analysis of bone images taken of a patient over a course of time by comparing the images to deduce positioning errors and/or to correct positioning errors for improved quantitative assessment of the bone.

9 Claims, 2 Drawing Sheets

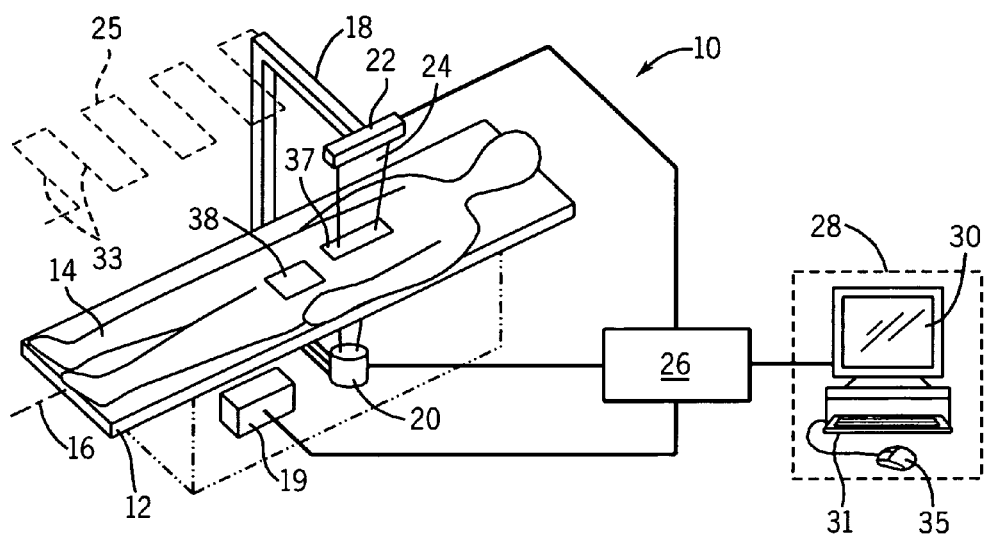
FIG. 1
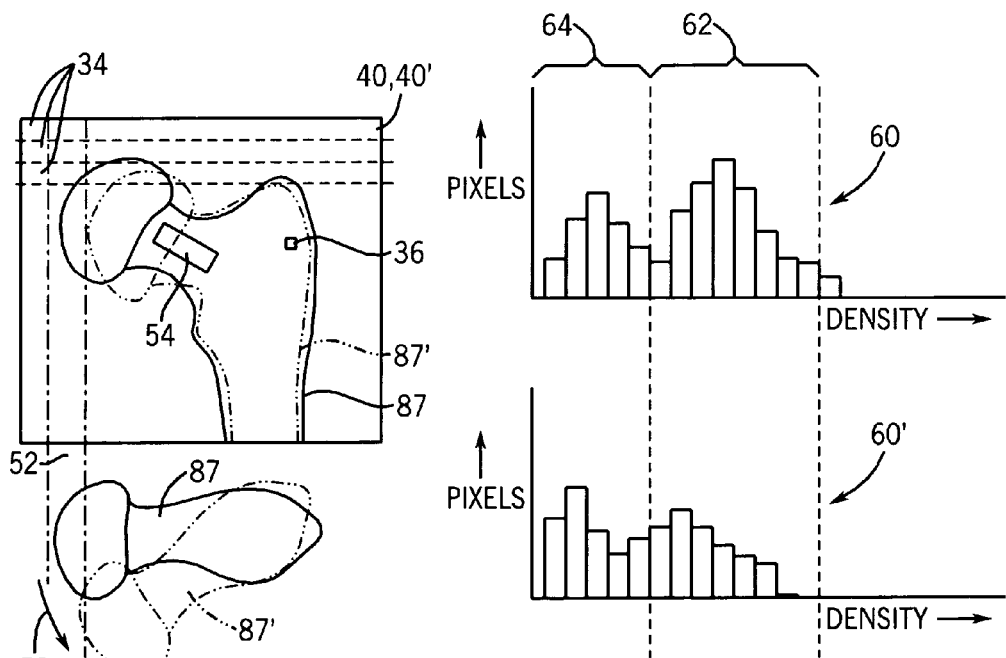
FIG. 2
FIG. 3

US 7,069,066 B2

BONE DENSITOMETER PROVIDING IMPROVED LONGITUDINAL STUDIES

CROSS-REFERENCE TO RELATED APPLICATIONS

This application is a continuation-in-part of U.S. application Ser. No. 10/065,109 filed Sep. 18, 2002, now U.S. Pat. No. 6,892,088, and hereby incorporated by reference.

STATEMENT REGARDING FEDERALLY SPONSORED RESEARCH OR DEVELOPMENT

BACKGROUND OF THE INVENTION

The present invention relates generally to x-ray bone densitometers for measuring bone health and particularly a densitometer adapted to monitor changes in bone health of a patient over a period of time.

X-ray bone densitometers make measurements at two x-ray energies to provide separate attenuation images of two basis materials, typically bone and soft tissue. The bone attenuation image is substantially free from attenuation caused by soft tissue allowing areal bone density (g/cm$^2$) to be accurately determined in vivo for assessments of bone strength and health. The bone attenuation image also provides improved definition of bone outlines, allowing measurements, for example, of bone morphology (e.g., vertebral height) such as may be useful for detecting crush fractures associated with osteoporosis.

Normally, such measurements evaluate a bone density within a region of interest (ROI) located within a bone (typically the neck of the femur or body of lower vertebrae) as referenced to one or more landmarks on the bone.

Often it is desired to detect changes in particular bones over time or over the course of a treatment. Positioning errors caused by changes in the position of the patient with respect to the densitometer can affect measurements of bone density in an ROI, by changing the apparent location of the landmarks used to locate the ROI and/or by changing the apparent density of the bone within the ROI by foreshortening caused by bone rotation.

It may be desired to evaluate localized changes in bone density, for example, in subregions distributed about the bone to detect subtle changes obscured when average bone density in a large area is examined. Detailed comparison of subregions of bone are also hampered by positioning errors which prevent direct comparison of bone images taken at different times.

BRIEF SUMMARY OF THE INVENTION

The present invention provides a computer-assisted bone densitometer in which software assesses changes in positioning of a patient between image acquisitions, alerting the operator to reposition the patient and/or correcting the acquired images for errors caused by mispositioning. Detection and correction of positioning errors allows more diagnostic information to be obtained from the images including not only improved measurements of regions of interest, but also novel measurements that investigate many subregions within the bone.

BRIEF DESCRIPTION OF THE DRAWINGS

FIG. 1 is a simplified perspective view of a bone densitometer performing a posterior-anterior or lateral scan of a patient with a fan beam under the control of a computer;

FIG. 2 is a depiction of foreshortening of a femur caused by rotation of the femur about a femur axis;

FIG. 3 is histograms of the femur and foreshortened femur of FIG. 2 showing determination of mispositioning of the patient by histogram area comparison;

DETAILED DESCRIPTION OF THE PREFERRED EMBODIMENT

Figure 4:
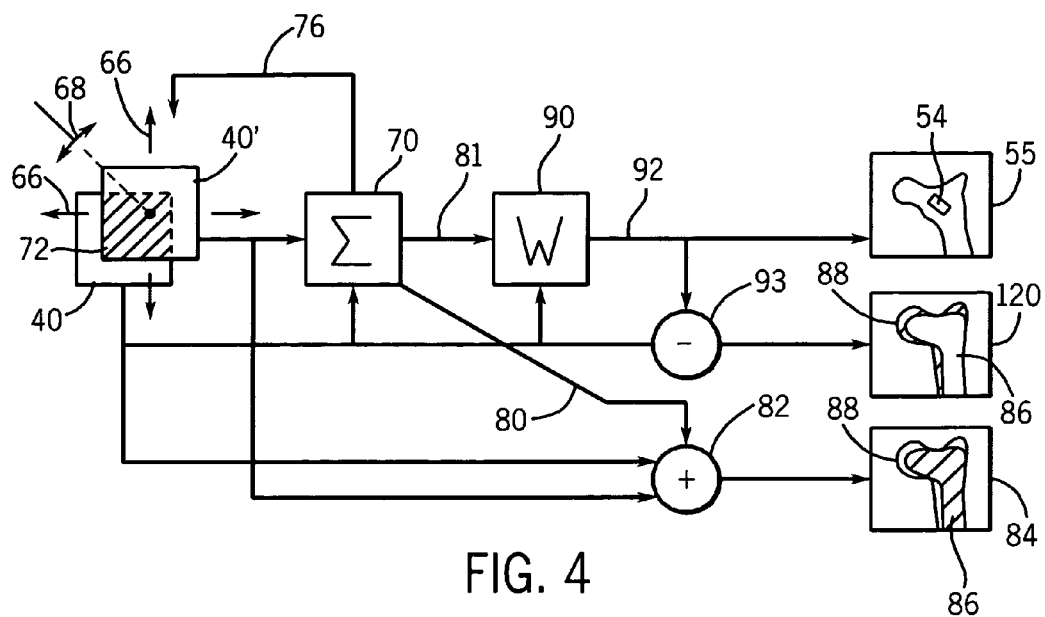
FIG. 4 is a block diagram showing the processing steps of comparing two bone images taken at different times to determine mispositioning of the patient and to correct distortions in the images for accurate inter-image comparison.

Referring now to FIG. 1, a bone densitometer 10 includes a patient table 12 providing a horizontal surface for supporting a patient in a supine or lateral position along a longitudinal axis 16.

A C-arm 18 has a lower end positioned beneath the patient table 12 to support an x-ray source 20 and an upper end positioned above the patient table 12 supporting an x-ray detector 22. The x-ray source 20 and x-ray detector 22 may be moved in a raster pattern 25 so as to trace a series of transverse scans 33 of the patient during which dual energy x-ray data are collected by the x-ray detector 22. This raster motion is produced by actuators under control of a translation controller 19 according to methods well understood in the art.

In the preferred embodiment, the x-ray source 20 provides two x-ray energies and the x-ray detector 22 is a multi-element CZT detector providing for energy discrimination. However, other methods of dual energy measurement including those providing for rotating filter wheels or variations in x-ray tube voltage may also be used.

The x-ray source 20 produces a fan beam 24 whose plane is parallel to the longitudinal axis 16. The raster pattern 25 is adjusted so that there is a slight overlap between successive scan lines of the fan beam 24.

The x-ray source 20, x-ray detector 22, and translation controller 19 communicate with, and are under the control of, computer 26 which may include both dedicated circuitry and one or more processors having the ability to execute a stored program, portions of which will be described in detail below. The computer 26 communicates with a terminal 28 including a display 30 and a keyboard 31 and a cursor control device such as a mouse 35 allowing for operator input and the output of text and images to the operator as is well understood in the art.

In operating the bone densitometer 10, the computer 26 will communicate with the translation controller 19 to scan a region of the patient in one or more transverse scans 33 during which a number of scan lines 34 of data will be collected, each with a different ray of the fan beam 24. These data will include attenuation measurements at two distinct energy levels. At each data point, the two measurements may be combined to produce separate bone and soft tissue images.

Referring now also to FIG. 2, a bone image 40 associated with a scan of the femur that may be composed of data of a variety of scan lines 34 associated with each of the rays detected by the x-ray detector 22. Bone density of other skeletal sites (for example, the lower lumbar vertebrae or the forearm) also may be measured. The measurements of each scan line produce measurements at a set of discrete pixels 36 representing an areal bone density along the ray line of that measurement. The bone density may be mapped to a gray scale to present the bone image 40 on the terminal 28 to the operator.

In a typical study, images of one or both of two areas are obtained of a scan area 37 of the lower lumbar spine 89 producing bone image 40, or of scan area 38 of either proximal femur 87 producing bone image 40 shown in FIG. 4.

Referring still to FIG. 2, the densitometer 10 may provide a first bone image 40 taken at a first time and showing the femur 87 in a first position with the neck of the femur 87 generally parallel to the image plane. A second image 40' (indicated by dotted lines) may be obtained at a later time with the femur 87' in a second position rotated as indicated by arrow 50 with the neck of the femur extending out of the image plane and causing a foreshortening 52 in the image 40'.

A region of interest 54 may be positioned on one or both of these images 40 and 40' for a bone density assessment according to techniques well known in the art. The region of interest 54 may be manually or automatically positioned with respect to landmarks on the femur 87.

Referring now to FIGS. 2 and 3, pixels 36 of each of the images 40 and 40' are associated with a bone density value derived from dual energy measurements. These pixels 36 may be collected in corresponding histograms 60 for image 40 and histogram 60' for image 40', each histogram 60 and 60' sorting pixels 36 into vertical bars by density values indicated along the horizontal axis.

Such histograms, 60 and 60', allow the separation of pixels 36 into bone pixels within a range 62 and nonbone pixels 36 (soft tissue) within a range 64 typically based on analyses of peaks in the histograms 60 and 60'.

Detection of Patient Positioning Errors

In a first embodiment of the present invention, the areas of the histograms 60 and 60' within the range 62 are compared to give an estimate of the amount of bone in each of the images. The areas may be computed simply by counting the number of pixels in the range 62 for each histogram 60 and 60'. Significant difference between these areas indicates a mispositioning of the patient and may be signaled to the operator, for example, in the form of a message stating that the patient may need to be repositioned.

Referring now to FIG. 4 in a second embodiment, a more sophisticated comparison process provides first for an iterative translation 66 of image 40' with respect to image 40 and a rotation 68 of image 40' with respect to image 40 to maximize the correlation between bone pixels 36 in range 62 in the images 40 and 40' as performed by correlation engine 70. The correlation engine 70, which may be realized in software, generally tallies the number of bone pixels in range 62 that overlap with bone pixels in image 40 at each iteration. This and the previous tally is used to generate a translation/rotation signal 76 that guides the translation and rotation process, for example, in a hill-climbing algorithm to approach the best alignment. As will be understood to those of ordinary skill in the art, the maximum allowed amount of translation 66 and rotation 68 may be constrained according to predefined limits and the correlation only considers an area of overlap 72 of the images 40 and 40'.

The correlation engine 70 thus aligns the images within the image plane as closely as possible. When the best alignment is found, the correlation engine may send the amount of translation 66 and rotation 68 as indicated by line 80 to a superposition circuit 82 which receives the two images 40 and 40' and displays them superimposed as offset per display 84. This display 84 may distinguish areas of overlap by color or brightness with, for example, a first color or brightness 86 applied to areas where there is no overlap and a second color or brightness 88 applied to areas where there is overlap, in this way providing a clear visual indication to an operator of the misalignment of the bones in the images 40 and 40' so as to allow repositioning by the operator of the patient for rescanning image 40'.

Correction of Patient Positioning Errors

Referring still to FIG. 4, the shifted image 40' may alternatively be provided to a warping engine 90 as indicated by line 81 which also receives image 40 and warps image 40' without additional translation or rotation to better fit image 40 with respect to the pixels 36 identified as bone. This warping may use standard mesh warping techniques and may be conducted automatically or manually to produce a warp-corrected image 92 transforming image 40' to matching image 40 after translation and rotation have been completed.

Figure 5:
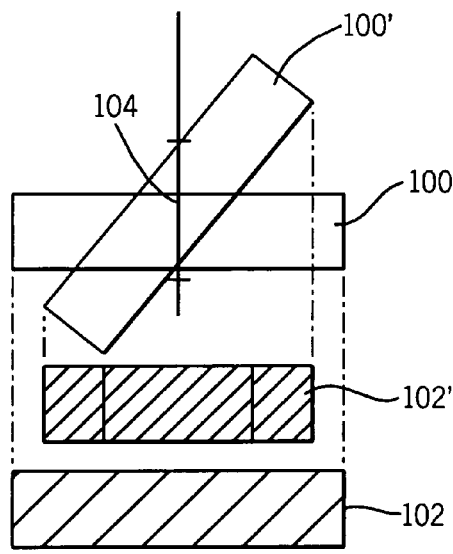
FIG. 5 is a schematic representation of a density artifact caused by bone foreshortening.

Referring now to FIG. 5, to the extent that the warping serves to correct for rotational foreshortening of the bone in the images 40 and 40', a density correction may be optionally performed. As shown in FIG. 5, an object 100 lying generally within the image plane provides an elongate image 102 having a given areal density value. A rotated object 100' of identical dimensions and material produces a shorter image 102' having a greater areal density value. This apparent change in areal density is caused by an increase in traversal length 104 of the x-rays passing through the object 100' as compared to object 100.

Figure 6:
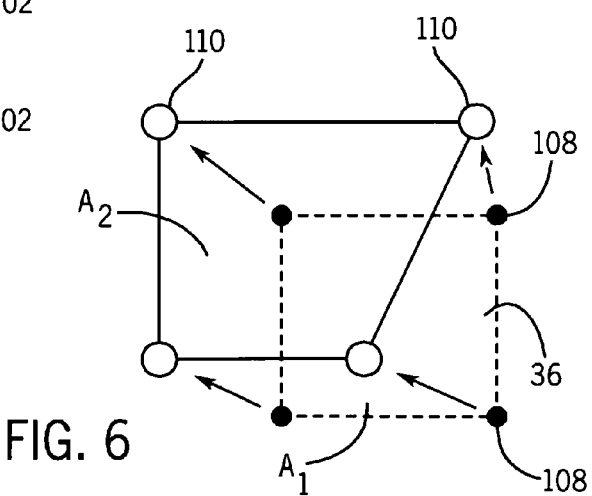
FIG. 6 is a geometric representation of a bone image pixel having an area caused by warping of the images such as may be compensated for mathematically.

Referring now to FIG. 6, generally this apparent increase in areal density may be corrected by dividing the density values of image 102' by the change of area effected by the warping engine 90. Thus, for example, if corner points 108 of a pixel 36 of original image 40' and having area $A_1$ are expanded to expanded corner points 110 after warping, a new area $A_2$ may be produced. The density value associated with the pixel 56 may be multiplied by $A_1/A_2$ to make this density correction. This correction may be performed by the warping engine 90.

The warp-corrected image 92 from the warping engine 90 may be subtracted from the original image 40 at block 93 to reveal a bone loss/gain display 120 providing not simply average bone density values in a region of interest, but a spatially resolved indication of bone loss or bone gain at different locations in the bone. This imaging requires extremely accurate registration of the images 40 and 40' provided by the present invention. This bone loss/gain display 120 may distinguish areas of bone loss or gain by color or brightness with, for example, a first color or brightness 86 applied to areas where bone has been gained and a second color or brightness 88 applied to areas where bone has been lost, in this way providing a clear visual indication to an operator of changes in the bone over time.

In an alternative embodiment, the warp-corrected image 92 having been corrected for rotation and density errors may be forwarded for subsequent processing including measurement of bone density within a predefined region of interest 54 in a display 55 of the corrected image 40'. Even without the correction for density errors, the correction of the geometric outlines of the bone can allow more accurate region of interest placement and thus, more accurate longitudinal studies of the patient.

It is specifically intended that the present invention not be limited to the embodiments and illustrations contained herein, but include modified forms of those embodiments including portions of the embodiments and combinations of elements of different embodiments as come within the scope of the following claims.

The invention claimed is:

1. A computer-aided bone densitometry system comprising:
    an x-ray source and detector opposable about a patient to produce signals indicating x-ray attenuation by bone of the patient;
    a computer receiving the signals and executing a stored program to:
    (a) collect a first and second bone density image at a first and second time;
    (b) determine a correspondence in bone areas in corresponding regions of the first and second bone density images; and
    (c) provide an indication to an operator of possible patient positioning error when a predetermined correspondence in bone areas is not found.

2. The computer-aided bone densitometry system of claim 1 wherein the indication to the operator is a signal.

3. The computer-aided bone densitometry system of claim 1 wherein the indication to the operator is an image depicting mismatch between corresponding regions.

4. The computer-aided bone densitometry system of claim 1 wherein the indication is an instruction to the operator suggesting a possible correcting repositioning of the patient.

5. The computer-aided bone densitometry system of claim 1 wherein the determination of correspondence in bone area uses a relative translation of the first and second bone density images in planes of the images to maximize a correspondence of the bone areas and wherein the determined correspondence is this maximized correspondence.

6. The computer-aided bone densitometry system of claim 1 wherein the determination of correspondence in bone area uses a relative rotation of the first and second bone density images in planes of the images to maximize a correspondence of the bone areas and wherein the determined correspondence is this maximized correspondence.

7. The computer-aided bone densitometry system of claim 6 wherein the determination of correspondence in bone area further uses a relative translation of the first and second bone density images in planes of the images to maximize the correspondence of the bone areas.

8. The computer-aided bone densitometry system of claim 1 wherein the bone density images are obtained with dual energy x-ray radiation.

9. The computer-aided bone densitometry system of claim 1 wherein the determination of correspondence in bone area applies a predetermined range to a pixel density histogram of the bone density images and wherein the areas of the pixel density histogram within the range is the correspondence.

* * * * *